(12) United States Patent
Rombach

(10) Patent No.: US 8,603,167 B2
(45) Date of Patent: Dec. 10, 2013

(54) INTRA-OCULAR ARTIFICIAL LENS WITH VARIABLE OPTICAL STRENGTH

(75) Inventor: Michiel Christiaan Rombach, Breda (NL)

(73) Assignee: Akkolens International B.V., Breda (NL)

( * ) Notice: Subject to any disclaimer, the term of this patent is extended or adjusted under 35 U.S.C. 154(b) by 902 days.

(21) Appl. No.: 11/914,260

(22) PCT Filed: May 11, 2006

(86) PCT No.: PCT/NL2006/050113
§ 371 (c)(1),
(2), (4) Date: Apr. 9, 2008

(87) PCT Pub. No.: WO2007/015640
PCT Pub. Date: Feb. 8, 2007

(65) Prior Publication Data
US 2009/0024214 A1    Jan. 22, 2009

(30) Foreign Application Priority Data

May 13, 2005   (NL) ..................................... 1029037

(51) Int. Cl.
*A61F 2/16*    (2006.01)
(52) U.S. Cl.
USPC .................... 623/6.32; 623/6.33; 623/6.37
(58) Field of Classification Search
USPC ........... 623/6.11, 6.23–6.24, 6.27–6.29, 6.32, 623/6.34, 6.37, 6.33
See application file for complete search history.

(56) References Cited

U.S. PATENT DOCUMENTS

| | | | | |
|---|---|---|---|---|
| 3,305,294 A | * | 2/1967 | Alvarez | 351/169 |
| 4,435,856 A | * | 3/1984 | L'Esperance | 623/6.34 |
| 4,892,543 A | * | 1/1990 | Turley | 623/6.13 |

(Continued)

FOREIGN PATENT DOCUMENTS

| | | |
|---|---|---|
| EP | 0162573 A2 | 11/1985 |
| EP | 1092402 A1 | 4/2001 |
| NL | 1025622 | 9/2005 |
| WO | 03000154 A2 | 1/2003 |

OTHER PUBLICATIONS

Search Report for Netherlands Patent Application No. 1029037; Dec. 14, 2005.

(Continued)

*Primary Examiner* — David H Willse
*Assistant Examiner* — Tiffany Shipmon
(74) *Attorney, Agent, or Firm* — Jason A. Bernstein; Barnes & Thornburg LLP

(57) ABSTRACT

An intra-ocular artificial lens with variable optical strength, having at least two optical elements, at least two of which are movable relative to each other in a direction extending transversely of the optical axis, wherein the optical elements have a form such that in different positions of the movable optical elements the artificial lens has a different optical strength, wherein the artificial lens has a fixed, positive optical basic strength wherein the variable optical strength caused by the relative movement of the movable elements is added to obtain the total optical strength of the artificial lens. Providing a different form results in the possibility of incorporating the greatest optical power in one of the optical elements. This optical element can then be optimized for the desired optical properties. The remaining optical element or the remaining optical elements can then be dimensioned for variation of the optical strength.

19 Claims, 3 Drawing Sheets

(56) References Cited

U.S. PATENT DOCUMENTS

| | | | |
|---|---|---|---|
| 4,994,082 A * | 2/1991 | Richards et al. | 623/6.32 |
| 5,824,074 A * | 10/1998 | Koch | 623/6.34 |
| 6,488,708 B2 * | 12/2002 | Sarfarazi | 623/6.34 |
| 6,609,793 B2 | 8/2003 | Norrby et al. | |
| 6,705,729 B2 | 3/2004 | Piers et al. | |
| 2001/0051826 A1 * | 12/2001 | Bogaert et al. | 623/6.23 |
| 2002/0105617 A1 * | 8/2002 | Norrby et al. | 351/177 |
| 2004/0158322 A1 * | 8/2004 | Shen | 623/6.33 |
| 2004/0236421 A1 * | 11/2004 | Lipshitz et al. | 623/6.27 |
| 2005/0267575 A1 * | 12/2005 | Nguyen et al. | 623/6.34 |
| 2006/0111776 A1 * | 5/2006 | Glick et al. | 623/6.34 |

OTHER PUBLICATIONS

Search Report for International Patent Application No. PCT/NL2006/050113; Oct. 24, 2006.

* cited by examiner

INTRA-OCULAR ARTIFICIAL LENS WITH VARIABLE OPTICAL STRENGTH

PRIORITY CLAIM

This patent application is a U.S. National Phase of International Application No. PCT/NL2006/050113, filed May 11, 2006, which claims priority to Netherlands Patent Application No. 1029037, filed May 13, 2005, the disclosures of which are incorporated herein by reference in their entirety.

FIELD

The present disclosure relates to an intra-ocular artificial lens with a variable optical strength. The present disclosure relates particularly to a lens comprising at least two optical elements, at least two of which are movable relative to each other in a direction extending transversely of the optical axis, wherein the optical elements have a form such that, in different relative positions, they together form a lens of different optical strengths.

BACKGROUND

Such artificial lenses are described in Netherlands Patent Application No. 1025622 for use as accommodating artificial lens, placed in the lens capsule after the removal of the natural eye lens or as adjustable refractive artificial lens which does not accommodate and optionally functions in combination with the natural lens.

In order to obtain the effect of the position-dependent variable optical strength, concessions must be made to the optical properties of the composite lens. This involves focus, wide field focus, the image conformity, the sensitivity to scattered light and other lens deviations and higher-order optical aberrations. The present disclosure provides measures with which the optical quality of such intra-ocular lenses is improved.

SUMMARY

Providing a different form of the optical elements results in the possibility of incorporating the greatest optical power in one of the optical elements. This optical element can then be optimized for the desired optical properties. The remaining optical element or the remaining optical elements can then be dimensioned for variation of the optical strength. A separation of the two functions, i.e., providing a relatively strong lens and providing a lens with variable strength of the optical elements, is hereby obtained so that both functions can be optimized independently.

According to a first exemplary embodiment, the artificial lens comprises two movable optical elements. This is a small number of optical elements which are both movable and which, due to their small number, can be easily accommodated in the structure of the eye.

The optical elements can have a mutually differing form. One of the two optical elements provides a high fixed optical strength, and contributes toward the optical variability. The remaining optical element only fulfills a function in the optical variability of the lens. It is also possible for each of the optical elements to make a mutually differing contribution toward the fixed strength.

It is also possible for both optical elements to have the same form. This entails that each of the optical elements contributes an equal share toward the fixed optical strength and to the variable optical strength. The optical elements are, of course, placed in mutually reversed manner.

Both optical elements preferably comprise a surface, one component of which satisfies the formula $z=S_U(x,y)=U(axy^2+bx^3/3)$. This means that the surfaces are curved according to a third order.

Instead of surfaces which satisfy the above stated formula, it is likewise possible to apply optical elements which are each provided with a surface which satisfies the formula $z=S_O(x,y)=O(cx^3+dy^3)/3$, a variation of the above basic formula. In this latter case, the direction in which the elements are mutually slidable will have to extend at an angle of 45° to the x-axis and the y-axis in order to obtain the variable strength. The constants c and d are not necessarily but preferably equal, so $c=d$, for a correct operation of the variable lens. This also relates to a surface curved according to the third order.

According to another exemplary embodiment, at least one of the two optical elements has a surface with a component which satisfies a formula for a lens with a fixed strength. An example of such a formula is the following formula: $z=S_C(x,y)=C(kx^2+ly^2)$. This is a formula for a parabolic lens with fixed (dioptric) strength. This fixed-strength lens defines the fixed refraction of the eye for vision at greater distance. The surfaces which satisfy the first stated formula herein provide the variability in the strength of the lens formed by the optical elements and, in this case, the parabolic lens provides an unchangeable basic strength of the lens. For a correct operation of the fixed lens, the constants k and l are not necessarily but preferably equal, so $k=l$.

For purposes of the present disclosure, a component of a surface means the situation in which a surface is curved according to two or more formulae. The optical elements according to the above stated exemplary embodiments after all have a part which contributes toward the fixed strength and a part which contributes toward the variable strength. Because each element has two surfaces, it is possible to form one of these surfaces in accordance with one of these formulae and to form the other surface in accordance with the other formula. It is also possible for both formulae to be applied on a single surface. Both formulae or algorithms herein form a constituent component of such a composite surface.

An even further distributed exemplary embodiment provides the measure that the artificial lens has a fixed optical element with a fixed optical strength and two movable optical elements, wherein the fixed optical element has a form which differs from the form of each of the movable optical elements.

The fixed optical element fulfills the function of providing sufficient optical strength, while the two movable elements have the function of providing the variable optical function. Because the optical functions are completely separated in this exemplary embodiment, both functions can be optimized. From a production engineering viewpoint, it may be desirable to make both movable lens elements identical and to arrange them in the eye in mutually reversed manner. It is, however, also possible to make use of different optical elements.

The movable optical elements are preferably adapted to perform an equally large movement in opposite directions, and both movable optical elements have a surface with a component which satisfies the formula $z=U(axy^2+bx^3/3)$. As in the initially stated exemplary embodiment with only two elements, use is hereby made of surfaces according to the formula known from U.S. Pat. No. 3,305,294. In this exemplary embodiment with three optical elements, it is also possible to make use of surfaces in accordance with the formula, wherein a movement at an angle of 45° is possible.

According to a preferred exemplary embodiment, at least one of the optical elements has a surface with a component which satisfies a formula for a lens with a fixed strength. An example of such a formula is the following formula: $z=S_C(x,y)=C(kx^2+ly^2)$. It is, of course, desirable to arrange this or these surfaces on the optical element with a fixed strength. It is only then that a complete uncoupling of the fixed and variable optical elements is obtained.

A subsequent exemplary embodiment provides the measure that, of the three optical elements of the above stated exemplary embodiment, all functional for the variation in optical strength, a first optical element has a surface which satisfies the formula $z=S_F(x,y)=h_1+2A(ex^2y^2+fx^4/6)$, that a second optical element has a surface which satisfies the formula $z=S_N(xy)=h_2+N(gx^2y^2+hx^4/6)$ and that a third optical element has a surface which satisfies the formula $z=S_P(x,y)=h_3-P(ix^2y^2+jx^4/6)$. The constants e and f are not necessarily but preferably equal, so e=f, for a correct operation of the variable lens, the constants g and h are not necessarily but preferably equal, so g=h, for a correct operation of the variable lens, and the constants i and j are not necessarily but preferably equal, so i=j, for a correct operation of the variable lens. This, therefore, involves surfaces of a fourth order.

This exemplary embodiment is improved when the optical element $S_F$ is fixed and when the other elements $S_N$ and $S_P$ are both movable relative to the first element and movable relative to each other. The constants should preferably also be equal, so N=P=A, for a correct optical operation of the lens. Additionally, two surfaces $S_N$ and $S_P$ can be positioned with the third surface $S_F$ complementary to the said two surfaces. This lens is perhaps less suitable for application in the eye since the lens consists of three elements and exhibits more significant optical aberrations and greater sensitivity to incorrect positioning of elements, such as tilting and undesired shifting relative to the optical axis compared to the variable lenses with two elements. It must be noted that, in this lens with three elements, the lens strength does not change in linear fashion with the shifting of the elements. This lens perhaps has advantages for specific technical applications.

The application of these lenses in accordance with the optics deviating from the original design as described in U.S. Pat. No. 3,305,294 can be not only as intra-ocular lens in the human eye, but also technical, such as telescopes and cameras, as well as for human vision, such as spectacle lenses, contact lenses and, as described above, different types of optionally accommodating intra-ocular lenses.

An optical element of the variable lens, optionally with an additional fixed lens, can also be incorporated in a pair of glasses, and the other optical element in a contact lens, optionally with an additional fixed lens. The whole construction is hereby arranged outside the eye, and multifocal vision is obtained when looking through different parts of the glasses via the contact lens. The possible drawback of this approach is having to wear not just glasses but a combination of contact lenses and glasses. It has been found that the optical quality of the combination surpasses the optical quality of, for instance, only a pair of standard multifocal glasses.

Further lens configurations are elucidated below; it is noted here that these configurations and other measures according to the present disclosure, such as the placing at diverse locations in the eye, can likewise be applied in the case of intra-ocular lenses wherein more than two lens elements are used.

For the function of the above described optical elements, their relative position is only important to the extent that their position must be taken into account in the dimensioning of the elements. It is thus possible, in principle, to place the elements at a relatively great mutual distance or close together, provided their relative position is taken into account in the dimensioning thereof. A preferred exemplary embodiment, therefore, teaches that all optical elements are placed close to each other. Not only can the elements then be easily placed as a single unit, but the short mutual distance between the optical elements results in a simpler and optically better optical design.

There can be reasons for placing the elements further apart. It is then desirable to combine the movable optical elements into a single unit, which can also entail optical advantages.

For the quality of the optics overall, it is generally advisable to position the lens function with the fixed strength as closely as possible in front of or behind the iris of the eye and to position the optical functions which cause the variation in strength as close together as possible. The function of the fixed strength and the variable function can be situated on the same elements, but do not necessarily have to be.

Yet another exemplary embodiment provides the measure that the intra-ocular lens is adapted for placing with the movable optical elements to the side of the cornea in an eye, outside the lens capsule. The placing with the movable elements on the outside has the advantage that the movable elements, on which adjusting or modifying operations must sometimes still be performed, are more readily accessible. In this exemplary embodiment, the lens does not function as an accommodating lens but as an adjustable refractive lens in combination with the natural eye lens or in combination with an intra-ocular artificial lens of fixed optical strength.

Yet another exemplary embodiment provides the measure that the fixed optical element is adapted for placing in the lens capsule in the eye. The space left free in the lens capsule after removal of the natural eye lens can be used here.

All the above stated lenses have optical aberrations. In order to reduce these aberrations as much as possible, a first exemplary embodiment proposes such an intra-ocular eye lens, wherein one of the surfaces of one of the optical elements is provided with a correcting surface which satisfies the formula:

$$z = S(x,y) + \frac{r^2}{R\left\{1+\sqrt{1-(1+k)\times(r/R)^2}\right\}}$$

for dependent correction of optical aberrations, and $$z = S(x,y) + a_1 r^4 + a_2 r^6 + \ldots + a_n r^{(2x+2)}$$

for independent correction of higher order aberrations, including spherical aberrations by $a_2 r^4$ or the combination of both methods by $$z = S(x,y) + \frac{r^2}{R\left\{1+\sqrt{1-(1+k)\times(r/R)^2}\right\}} + a_1 r^4 + a_2 r^6 + \ldots + a_n r^{(2n+2)}$$

U.S. Pat. Nos. 6,609,793 and 6,705,729 describe several aspects of the corrections, in particular the $a_1 r^4 + a_2 r^6$ term for correction of single monofocal intra-ocular lenses.

Yet another exemplary embodiment provides the measure that at least one of the optical elements is provided with a correction term of one of its surfaces, which correction term corresponds with the formula $z=S_c(x,y)=C(mx^2-ny^2)$, in which k=1, and which formula can be used for correction of astigmatism, a commonly occurring optical aberration of the eye. The constants m and n are not necessarily but preferably equal, so m=n, for a correct operation of the variable lens.

The present artificial lenses can also be combined with prolate lens designs, wherein the change in the diameter of the iris can be included in the accommodation process.

An alternative manner of mathematical representation is the following: Lenses can be designed according to spherical, parabolic and hyperbolic projections via standard Zernike formulae. The artificial lenses described here can be optimized by making use of these projections and combinations thereof in the same optical surfaces.

The above described lenses formed by two optical elements can be radially superimposed. This is possible in accordance with, though not exclusively in accordance with:

$$x = -\left(R + A(R\phi)(R\theta)^2 + \frac{A(R\phi)^3}{3} + DR\phi + E\right)\cos(\theta)\sin(\phi)$$

$$y = -\left(R + A(R\phi)(R\theta)^2 + \frac{A(R\phi)^3}{3} + DR\phi + E\right)\sin(\theta)$$

$$z = R - \left(R + A(R\phi)(R\theta)^2 + \frac{A(R\phi)^3}{3} + DR\phi + E\right)\cos(\theta)\cos(\phi)$$

Such a lens can provide significant optical advantages in the eye since a number of inherent optical shortcomings are thus compensated.

The above described lenses can also be superimposed on a body of revolution of a conical section in accordance with, though not exclusively in accordance with:

$$z = \frac{cx^3}{3} + cxy^2 + E + Dx + \frac{c_2 y^2}{1 + \sqrt{1 - k_2 c_2^2 y^2}} + \frac{c_3 x^2}{1 + \sqrt{1 - k_3 c_3^2 x^2}}$$

which is a variation of the above stated correction formulae.

Lenses can also be designed according to the above stated principle; the lenses have an equivalent optical strength according to a conical body of revolution, in accordance with, though not exclusively in accordance with, as a variation of the above stated formulae for corrections:

$$z = \frac{cx^3}{6} + \frac{1}{40}c^3 kx^5 + \frac{1}{2}cxy^2 + \frac{1}{12}c^3 kx^3 y^2 + \frac{1}{8}c^3 kxy^4 + E + Dx$$

When a lens with a fixed optical strength is placed on only one of the optical elements, the optical axis shifts when the optical elements shift. It is possible to place the optical axis closer to the fovea or even on the fovea during accommodation, since the fovea does not lie on the optical axis. This effect of shifting of the optical axis during accommodation is unique for the lens types described here. Other intra-ocular lens types, including monofocal lenses, must be adjusted so that the optical axis contacts the fovea.

A standard lens of fixed strength does not correct the projection on the retina for spherical aberrations of the eye, for instance, cylindrical and higher-order aberrations. Cylindrical aberrations and other aberrations occur generally and are usually compensated relatively easily today with glasses or contact lenses. The present disclosure of an accommodating intra-ocular lens makes glasses unnecessary, however, and aberrations will, therefore, preferably also have to be corrected by the intra-ocular lens. Several types of cylindrical intra-ocular lenses for correction of cylindrical deviations are commercially available but not in general use; the patient still wears glasses after implantation of an artificial lens with fixed strength, and aberrations can also be corrected easily with these glasses. A cylindrical correction can, however, be added to the present intra-ocular lens with two shifting optical elements. Other higher-order corrections can also be incorporated into the optical design on one or more optical surfaces.

As already described above in Netherlands Patent Application No. 1025622, it is desirable when the optical elements are provided with a strengthening edge. This edge will, in many cases, be manufactured from the same transparent material as the material from which the optically active part of the optical element is manufactured. The result hereof is that light incident on this edge is deflected by the edge, and that after deflection the light disrupts the normal desired propagation of rays. In order to avoid this drawback, a particular exemplary embodiment proposes that at least one of the optical elements comprises a strengthening edge with a form which is at least partly such that light striking this edge is deflected outward.

For sufferers of some eye conditions, such as macular degeneration, it is desirable when the image is cast onto a healthy part of the retina. The eye lens is preferably adapted for this purpose to cast an image onto a position on the retina deviating from the optical axis. An optically desirable way in which this measure can be implemented is to provide a prism of at least one of the optical elements.

Yet another exemplary embodiment provides the measure that at least two of the optical elements are provided with markings for the purpose of facilitating the relative positioning of the optical elements. This measure is important during placing and positioning of the optical elements. This measure relates to all elements with extremely small dimensions, the positioning of which must be particularly precise, since the positioning has a great influence on the quality of the image observed by the patient.

For relative positioning of the optical elements in a first direction transversely of the optical axis, the markings comprise linear structures extending in a first direction. It is hereby possible to relatively position the optical elements in a first direction transversely of the optical axis. For relative positioning in the same plane in the first direction, the markings comprise linear structures extending in a second direction, transversely of the first direction. It is noted here that linear structures extending in one direction provide a reference in the direction perpendicular to that of the linear structures. Alternatively or additionally to the foregoing measures, the markings comprise radially extending linear structures. It is hereby possible to determine the relative rotation position of the optical elements.

The positioning of the lens elements by the ophthalmic surgeon in order to achieve a correct refraction can also be carried out during the lens implantation operation, optionally simultaneously with a refractive measurement of the eye, during the operation and as reference for a correct adjustment of basic lens strength and positioning.

The present disclosure describes several exemplary embodiments of the present invention.

One aspect of the present disclosure provides an intra-ocular artificial lens with variable optical strength, comprising at least two optical elements, at least two of which are movable relative to each other in a direction extending transversely of the optical axis, wherein the optical elements have a form such that in different positions of the movable optical elements the artificial lens has a different optical strength, characterized in that wherein the artificial lens has a fixed, positive optical basic strength, wherein the variable optical strength caused by the relative movement of the movable elements is added to obtain the total optical strength of the artificial lens.

BRIEF DESCRIPTION OF THE DRAWINGS

The present disclosure will be elucidated hereinbelow on the basis of the accompanying figures, in which.

DETAILED DESCRIPTION

Figure 1:
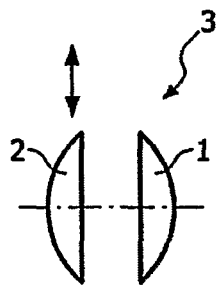
FIG. 1 shows a cross-sectional view of a configuration of two optical elements which together form an intra-ocular lens according to the prior art.

FIG. 1 shows a configuration of two optical elements 1, 2, which together form an intra-ocular lens 3. Both elements are movable in the direction transversely of the optical axis. The optical elements have a design such that the optical elements impart a different value to lens 3 in different relative positions. The embodiment shown here is the subject of Netherlands Patent Application No. 1025622. According to the simplest embodiment of the intra-ocular lens described in this document, the two optical elements are identical.

Figure 2:
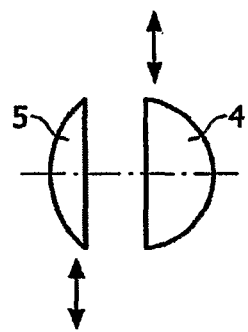
FIG. 2 shows a cross-sectional view of a first embodiment of an intra-ocular eye lens according to the prior art.

This is, however, by no means necessary; FIG. 2, for instance, shows an embodiment wherein the two optical elements 4 and 5, which are different, are applied; the rear optical element 5 has a greater volume and contributes more toward the optical strength than front element 4. The large element 5 can be optimized for its function.

Figure 3:
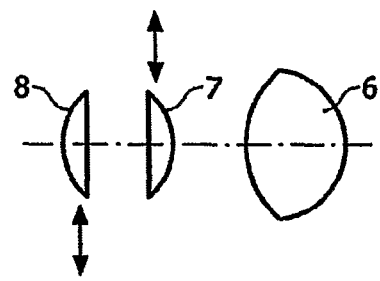
FIG. 3 shows a cross-sectional view of a second embodiment of an intra-ocular eye lens according to the prior art.

An even more highly optimized configuration is shown in FIG. 3; three optical elements are applied here, i.e., a fixed element 6 and two movable optical elements 7, 8. Fixed optical element 6 contributes most toward the optical strength, while both elements 7, 8 movable in the transverse direction provide for the accommodating function due to their variability. This specialization provides the option of optimizing each of the elements for the earmarked function.

Figure 4:
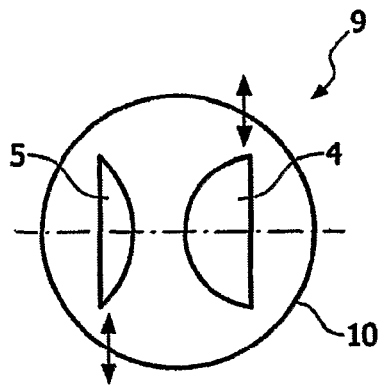
FIG. 4 is a variant of the first embodiment shown in FIG. 2.

In the above embodiments, the mutual distance in the direction of the optical axis is not relevant. The embodiment of FIG. 4 shows how two different elements 4, 5 are combined into a single unit 9. This unit can be accommodated integrally in capsule 10 of the natural eye lens.

Figure 5:
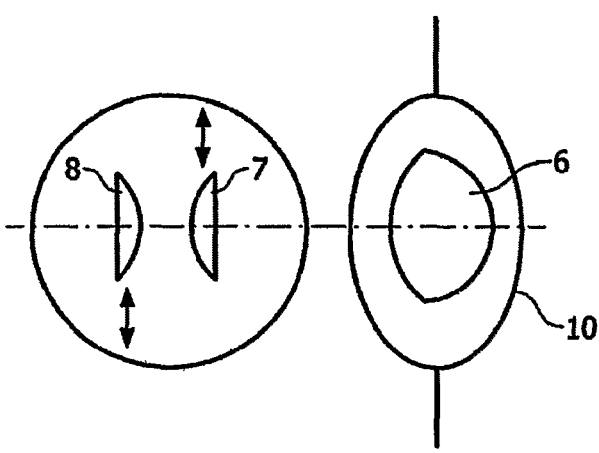
FIG. 5 is a variant of the second embodiment shown in FIG. 3.

It is, however, also possible for the optical elements to be divided into two groups, as shown in FIG. 5. Fixed element 9 is preferably accommodated in capsule 10 of the natural eye lens, and the movable optical elements 7, 8 are arranged together at a different location inside the eye. Such a division of the optical elements into two groups is otherwise also possible when only two elements are applied.

Figure 6:
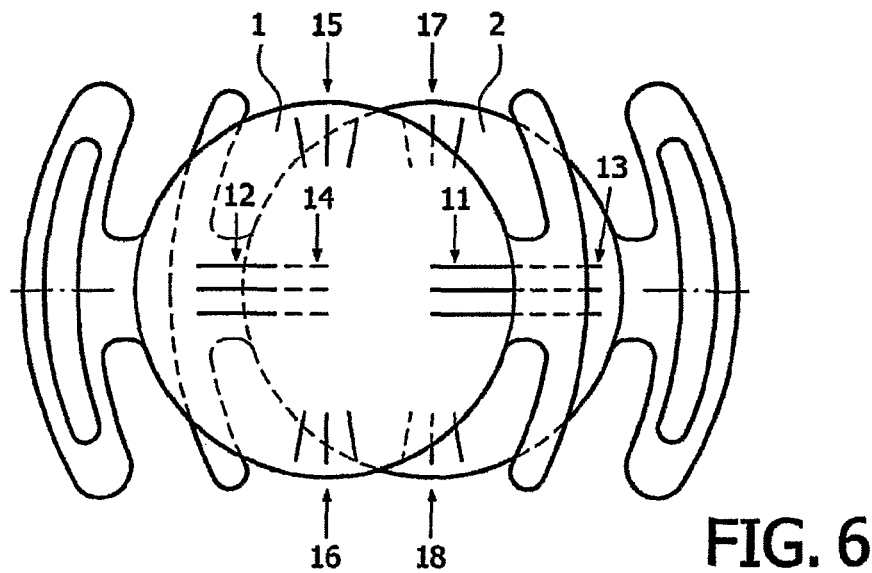
FIG. 6 shows a schematic top view of a combination of optical elements provided with a marking.

FIG. 6 shows a combination of two optical elements 1, 2, which are both provided with markings. These markings are formed by a series of stripes 11 on a first side of the first optical element 1 and a series of stripes 12 on the second side of optical element 1. Stripes 11, 12 extend only over a short distance on either side of the center of optical element 1 so as to disrupt the propagation of rays through optical element 1 as little as possible. Stripes 11, 12 are formed by irregularities which are arranged on optical element 1 and are visible to the human eye, such as stripes printed with ink, lasered-in irregularities or ribs or grooves in the material of optical element 1. The second optical element 2 is provided with similar stripes 13, 14 respectively. A correct position of optical elements 1 and 2 in a first direction can be guaranteed by causing overlap of stripes 11 and stripes 13 and overlap of stripes 12 and stripes 14. It is pointed out here that a single stripe is sufficient per se to provide a reference, but that a plurality of stripes facilitates the positioning process.

Elements 1, 2 are moreover each provided with an array of radially extending stripes 15 and 16, and 17 and 18, respectively, which serve to determine the mutual rotation position. They can otherwise also be used to determine the relative translation position in the direction parallel to that of stripes 11-14. It is also possible to use specific stripes extending parallel to each other for this purpose.

It must be noted that in all figures a complex arcuate surface is shown schematically by a single, randomly chosen convex surface. A stronger convexity herein illustrates the addition of a stronger lens of fixed value to the arcuate surface.

Figure 7:
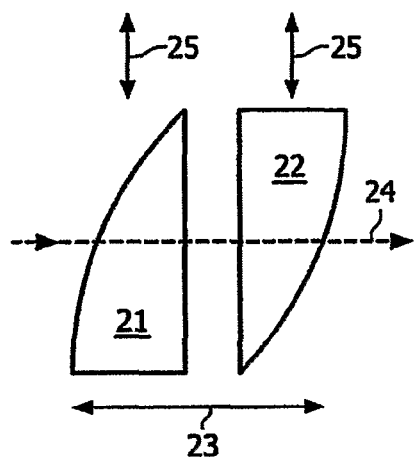
FIG. 7 shows a cross-sectional view of a lens configuration of two identical optical movable elements.
Figure 8:
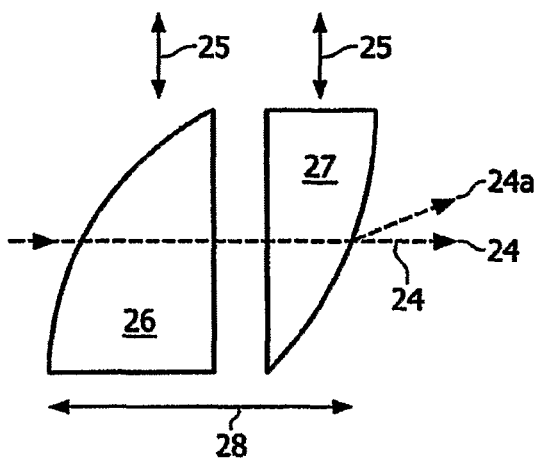
FIG. 8 shows a cross-sectional view of a lens configuration with two different optical movable elements.

FIG. 7 shows a configuration of two optical elements 21, 22 which together form an intra-ocular lens 23. Both elements are movable in the direction transversely of optical axis 24, as indicated by arrows 25. Optical elements 21, 22 have a design such that they impart a different dioptric optical value to lens 23 in different relative positions. A lens of a fixed strength is divided evenly over both optical elements. The embodiment of FIG. 8 shown here is the subject of Netherlands Patent Application No. 1025622. According to the simplest embodiment of the intra-ocular lens described in this document, the two optical elements are identical.

Identical elements are by no means necessary, however; FIG. 8, for instance, shows an exemplary embodiment wherein the two optical elements 26 and 27 are applied which are different; front optical element 26 has a greater optical fixed strength and contributes more toward the optical strength of the whole element 28 than rear element 27. Both elements 26, 27, however, make an equal contribution toward the variable component of the optical strength. Also shown here is that, if different moving optical elements are used, the optical axis has a deviant angle 24a during the accommodation process.

Figure 9:
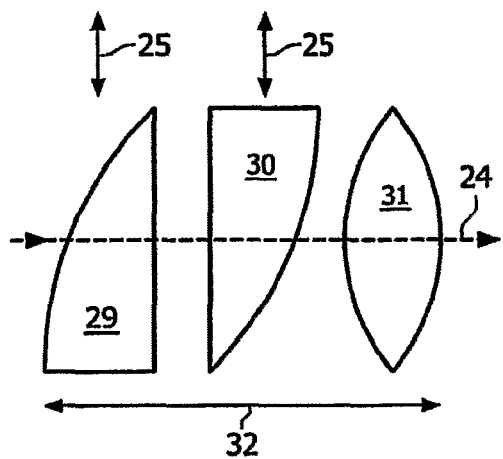
FIG. 9 shows a cross-sectional view of a lens configuration with two identical movable elements and a fixed optical element.

FIG. 9 shows that the lens with the two identical elements 29, 30 can be combined with a strong, unmoving optical element with the function of a fixed lens 31, which can optionally be incorporated in a construction with movable elements 29, 30. The combined lens 32 is formed by all three optical elements 29, 30, 31. This specialization provides the option of optimizing each of the elements for the earmarked function.

Figure 10:
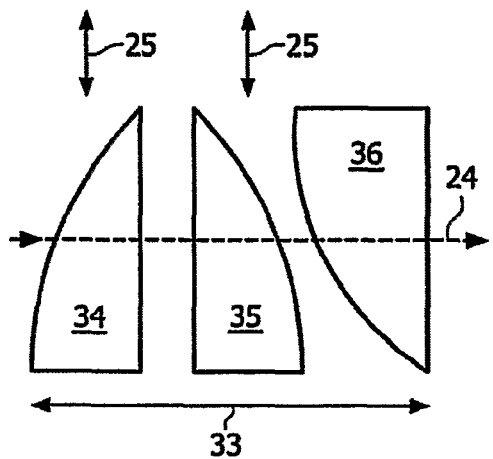
FIG. 10 shows a cross-sectional view of a lens configuration with three arcuate elements, two of which are movable.

In FIG. 10, a lens 33 with variable strength is formed by three arcuate elements 34, 35 and 36, of which 34 and 35 are positioned additionally relative to 36, which is positioned complementarily relative to 34 and 35. In this configuration, element 34 and element 35 carry out the movement. For the slightly deviating mathematical representation of this configuration we refer to the text.

Figure 11:
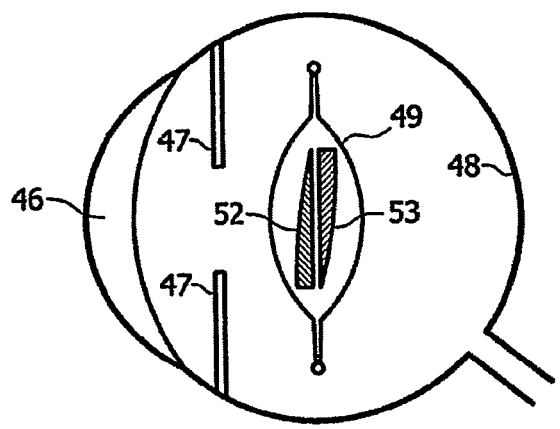
FIG. 11 shows a schematic cross-sectional view of a first configuration of different optical elements in the eye.

A schematic cross-section of the eye with cornea 46, iris 47 and retina 48 is shown in FIG. 11. For intra-ocular applications, the optical elements 52, 53 can be placed in lens capsule 49, with optionally identical optical elements as shown in FIG. 11. In the present exemplary embodiment these optical elements 52, 53 in lens capsule 49 serve to correct the refraction of the eye and to carry out the accommodating function.

Figure 12:
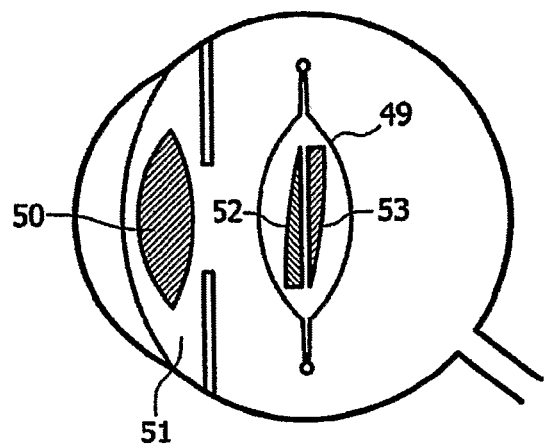
FIG. 12 shows a schematic cross-sectional view of a second configuration of different optical elements in the eye.

In FIG. 12, the movable optical elements are placed in lens capsule 49, and an optical element of fixed strength 50 is placed in anterior chamber 51. These are obvious and practical configurations, but it is also possible to envisage other configurations, for instance, arranging the lens with fixed strength 50 in the posterior chamber as well. In the present exemplary embodiment these optical elements in the lens capsule only serve for carrying out the accommodating function.

Figure 13:
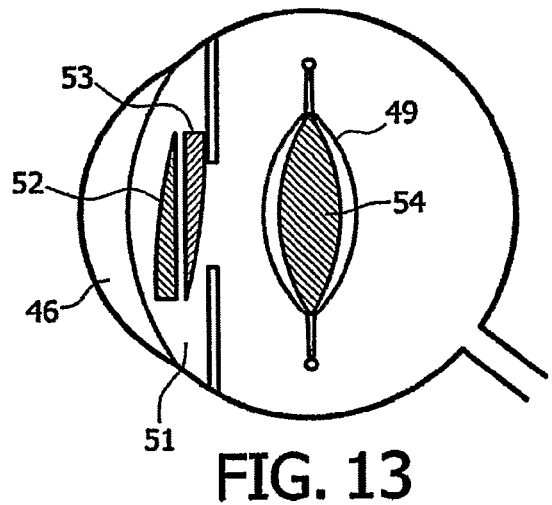
FIG. 13 shows a schematic cross-sectional view of a third configuration of different optical elements in the eye.

In FIG. 13, the variable lens with elements 52 and 53 is applied as a non-accommodating but adjustable refractive intra-ocular lens, in this case placed in anterior chamber 51. This variable lens is then adjusted by the ophthalmic surgeon at long intervals so as to adjust the refraction of the eye to new conditions, and the variable lens functions with a lens 54 which is situated in the lens capsule. This lens 54 can certainly also be the natural eye lens.

All patents, patent applications and publications referred to herein are incorporated by reference in their entirety.

The invention claimed is:

1. An intra-ocular artificial lens with variable optical strength, comprising:
   at least a first and a second optical element which are movable relative to each other in a direction extending transverse to the optical axis; and,
   a third optical element having a fixed focal strength,
   wherein the first and the second optical element have a form such that in different positions of the movable optical elements the artificial lens has a different focal strength, and
   wherein the first and the second optical elements each have a surface having a component having a component curved to a third order.

2. The intra ocular lens of claim 1, wherein the lens is adapted to be placed with its movable optical elements outside the lens capsule.

3. The intra-ocular artificial lens of claim 2, wherein the artificial lens is adapted for placing with the movable optical elements in front of the iris in an eye.

4. The intra ocular lens of claim 1, wherein the lens is adapted to be placed with the movable optical elements inside the lens capsule.

5. The intra-ocular artificial lens of, claim 1, wherein the optical element with the greatest optical strength is placed closest to the iris.

6. The intra-ocular artificial lens of claim 1, wherein at least two of the optical elements are provided with markings for the purpose of facilitating the relative position determination of the optical elements.

7. An intra-ocular artificial lens with variable optical strength, comprising:
   a first and a second optical element which are movable relative to each other in a direction extending transverse to the optical axis,
   wherein the first and the second optical element have a form such that in different positions of the movable optical elements the artificial lens has a different focal strength,
   wherein the first and the second optical elements each have a surface having a component curved to a third order, and
   wherein at least the first optical element has a surface with a component adding a fixed optical strength to the first optical element.

8. An intra-ocular artificial lens with variable optical strength, comprising:
   a first and a second optical element which are movable relative to each other in a direction extending transverse to the optical axis;
   a third optical element
   wherein each of the first, second and third optical elements comprises a surface component curved according to a fourth order, and
   wherein at least one of the optical elements has an additional surface component which satisfies a formula for a lens with a fixed strength.

9. The intra-ocular artificial lens of claim 8, wherein the surface components curved to a third order satisfy the formula $z=U(axy^2+bx^3/3)$, wherein x, y and z represent distances along x, y and z axes of a rectangular coordinate system, U is the amplitude coefficient in [units of length]$^{-2}$ specifying the degree of variation of optical strength, and a and b determine the relative curvatures of the resulting variable surface in the planes $x=0$ and $y=0$, respectively.

10. The intra-ocular artificial lens of claim 8, wherein the first optical element has a surface component curved to a fourth order satisfying the formula $z=S_F(x,y)=h_1+2A(ex^2y^2+fx^4/6)$, wherein the second optical element has a surface components satisfying the formula $z=S_N(x,y)=h_2+N(gx^2y^2+hx^4/6)$ and wherein the third optical element has a surface satisfying the formula $z=S_P(x,y)=h_3-P(ix^2y^2+jx^4/6)$.

11. The intra-ocular artificial lens of claim 8, wherein only the first optical element has an optical surface with a component adding a fixed optical strength.

12. The intra-ocular artificial lens of claim 8, wherein the second optical element has an optical surface adding a fixed optical strength.

13. The intra-ocular artificial lens of claim 8, wherein the optical strengths of the optical surfaces added to the first and the second optical elements are equal.

14. The intra-ocular artificial lens of claim 8, wherein the optical strengths of the optical surfaces added to the first and the second optical elements are unequal.

15. The intra-ocular artificial lens of the claim 8, wherein the lens comprises at least one surface comprising at least two surface components.

16. The intra-ocular artificial lens of claim 15, wherein at least one of the optical surfaces comprises an optical surface component having a fixed strength and an optical surface component curved to a third or fourth order.

17. The intra-ocular lens of claim 15, wherein at least one of the optical surfaces comprises a correcting surface component adapted to correct an optical aberration.

18. The intra-ocular artificial lens of claim 17, wherein at least one of the surfaces of one of the optical elements is provided with a correcting surface which satisfies the formula:

$$z = \frac{cx^3}{3} + cxy^2 + E + Dx + \frac{c_2 y^2}{1+\sqrt{1-k_2 c_2^2 y^2}} + \frac{c_3 x^2}{1+\sqrt{1-k_3 c_3^2 x^2}}$$

19. An intra-ocular lens of claim 15, wherein the correcting surface component is adapted to correct astigmatism.

* * * * *